US006294682B1

(12) United States Patent
Rauleder et al.

(10) Patent No.: US 6,294,682 B1
(45) Date of Patent: Sep. 25, 2001

(54) ALKOXIDES WITH ALKALINE EARTHS AND TITANIUM, ZIRCONIUM AND/OR HAFNIUM, THEIR PRODUCTION AND USE

(75) Inventors: Hartwig Rauleder, Rheinfelden; Burkhard Standke, Lorrach; Michael Horn; Hans-Joachim Kotzsch, both of Rheinfelden; Hans-Gunther Srebny, Dulmen-Rorup, all of (DE)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/077,671
(22) PCT Filed: Dec. 3, 1996
(86) PCT No.: PCT/EP96/05359
  § 371 Date: Jun. 19, 2000
  § 102(e) Date: Jun. 19, 2000
(87) PCT Pub. No.: WO97/20790
  PCT Pub. Date: Jun. 12, 1997

(30) Foreign Application Priority Data

Dec. 6, 1995 (DE) .............................. 195 45 444

(51) Int. Cl.$^7$ .............. C07F 19/00; C07F 7/00; D21H 25/00

(52) U.S. Cl. ................................. 556/28; 556/54; 162/79; 8/119

(58) Field of Search .................... 556/28, 54; 162/79; 8/119

(56) References Cited

U.S. PATENT DOCUMENTS

| | | | |
|---|---|---|---|
| 3,676,182 | * 7/1972 | Smith | 117/60 |
| 4,178,300 | * 12/1979 | van der Berg | 260/413 |
| 4,333,881 | * 6/1982 | Greco et al. | 260/429 R |
| 4,609,755 | * 9/1986 | Farrar | 560/217 |
| 5,322,558 | * 6/1994 | Wittekind et al. | 106/257.24 |

* cited by examiner

Primary Examiner—Porfirio Nazario-Gonzalez

(57) ABSTRACT

The invention concerns solutions of alkoxides containing titanium and/or zirconium and/or hafnium and magnesium and/or calcium and/or strontium and/or barium of general formula (I): $[M^{II}(OR)_{2-y}(OR^1)_y]_n[M^{IV}(OR^1)_{4-z}(OR)_2]$, in which: $M^{II}$ means magnesium and/or calcium and/or strontium and/or barium; $M^{IV}$ titanium and/or zirconium and/or hafnium; R is an alkyl group with 1 to 18 carbon atoms; $R^1$ is an alkyl group with 1 to 18 carbon atoms; y has a value of between 0 to 2; z has a value of 0 and 4; and n is a number between 0.001 and 3, with the exception that n cannot be 1 when y is 2 and z is 0, or when y is 0 and z is 4. The invention further concerns the production of these alkoxides and their use.

8 Claims, No Drawings

ALKOXIDES WITH ALKALINE EARTHS AND TITANIUM, ZIRCONIUM AND/OR HAFNIUM, THEIR PRODUCTION AND USE

The present invention relates to solutions of alkoxides containing titanium or zirconium or hafnium and magnesium or calcium or strontium or barium, a process for their preparation, and their use.

Metal alcoholates and metal acid esters find a variety of applications in technical fields.

The preparation of Ziegler catalysts generally proceeds from metal alcoholates, a procedure which is known as such. Catalysts of this type containing vanadium or chromium are frequently employed in olefin polymerization in suspension or in the gas phase, although such catalysts containing vanadium or chromium are hardly desirable from a toxicological point of view.

Cellulose-containing materials, e.g., paper containing aluminum sulfate, are subject to degradation by acid. Large irreplaceable historic file and book stocks are threatened by destruction due to acid attack.

The use of lyes containing alkali or alkaline earth alcoholates as a neutralizing component for the treatment of such cellulose-containing materials has been described (U.S. Pat. No. 3,676,182) as early as 1966. As a preventive measure against excessive basicity, such a treatment may also contain predominantly acidic alkoxides, for example, of the elements aluminum, tin, boron, titanium or zirconium, although such measure is not detailed any further in the description or examples of the above mentioned U.S. Patent.

The preparation of complex alkoxides from the elemental metals, such as aluminum, magnesium, calcium, is known from basic work by Meerwein and Bersin ("Untersuchungen über Metallalkoholate und Orthosäureester", Liebigs Ann. Chem. 476, 113–150). This method is not applicable to the elements titanium, zirconium and hafnium since a standstill of the reaction between a much more reactive alkali alcoholate and a titanic or zirconic ester on the level of low conversions has been described, and an even poorer reactivity could be predicted for alkaline earth alcoholates in connection with titanic or zirconic esters because of their reactivities which are anyway lower than that of the alkali alcoholates.

Our own studies have, indeed, shown that no formation of a compound occurs in common solutions or suspensions of alcoholates of the alkaline earth metals and of titanium or zirconium; the alcoholates employed are simultaneously present without reacting with one another. Even at the boiling temperature of the solution, no formation of complex alkoxides is observed when the solvent or suspension agent, e.g., hydrocarbons, such as hexane, heptane etc., aromatic hydrocarbons, e.g., xylene or toluene, or siloxanes, e.g., hexamethyldisiloxane, is removed under vacuum.

Indeed, the preservation method proposed at the time in U.S. Patent Specification No. 3,676,182 has not been applied beyond the experimental stage, in spite of great urgency, since it fails to meet a number of indispensible preconditions of such an application: for example, ensuring that the neutralizing agents, which often tend to be insoluble, are in a liquid form for a successful thorough treatment, i.e. for completeness of the paper impregnation, and especially harmlessness towards printing and stamping inks of the texts and illustrations, which must be preserved in a completely integral condition, and their bookbinding adjuvants.

DE-OS 41 38 750 discloses double alkoxides of the formula $Me^{I}(OR)_x \cdot Me^{II}(OR)_y$ wherein $Me^{I}$ corresponds to an element of Group 4 of the Periodic Table, aluminum or tin, and $Me^{II}$ corresponds to an alkali or alkaline earth element, and in addition, the OR groups may be derived from different kinds of alcohols, e.g., dihydric or polyhydric alcohols; thus, compounds of two alkoxides employed in a ratio of 1:1 and having the same alkoxide groups, such as $Al^{III}(OC_2H_5)_3 \cdot K^{I}(OC_2H_5)$ or $Sn^{IV}(OC_3H_7)_4 \cdot Mg^{II}(OC_3H_7)_2$ or $Zr^{IV}(O-C_2H_4-O)_2 \cdot Ca^{II}(O-C_2H_4-O)$, can be derived therefrom. Such double alkoxides are used as neutralizing agents, conveniently dissolved in an appropriate solvent (DE-OS 41 04 515), for example, alcohols, fluorohydrocarbons or fluorochlorohydrocarbons, naphtha hydrocarbons or siloxanes, for the large-scale deacidification of archives. There is a drawback in that the use of the above mentioned double alkoxides leaves evident powdery residues, for example, of the metal oxides or oxide hydrates, oxide hydroxides, the corresponding carbonates etc., after the large-scale deacidification. A further problem remaining unsolved is an improvement of mechanical stabilization of the paper sheets which are, as a rule, in a more or less impaired condition or already in beginning decomposition, which improvement is to be achieved simultaneously with the neutralization, if possible.

Thus, it has been the object of the present invention to provide mechanical stabilization of materials containing cellulose fibers in addition to the neutralization thereof, and a process for the preparation of a substance having such properties as to achieve this.

Surprisingly, it has been found that alkoxides of general formula I $$[M^{II}(OR)_{2-y}(OR^1)_y]_n \cdot [M^{IV}(OR^1)_{4-z}(OR)_z] \qquad (I)$$

wherein $M^{II}$ represents magnesium and/or calcium and/or strontium and/or barium; and $M^{IV}$ represents titanium and/or zirconium and/or hafnium;

R is an alkyl residue of from 1 to 18 carbon atoms; and $R^1$ is an alkyl residue of from 1 to 18 carbon atoms;

y takes a value of from 0 to 2; and z takes a value of from 0 to 4; and n is a number of between 0.001 and 3;

can be obtained by reacting at least one alkoxide of the elements magnesium and/or calcium and/or strontium and/or barium with at least one alkoxide of the elements titanium and/or zirconium and/or hafnium at a temperature which is in the range of the decomposition temperature of at least one of the alkoxides employed.

Substances which promote the formation of a melt can suitably be added to the reaction mixture of the individually employed alkoxides. In addition, the alkoxides of general formula I, which can be prepared by the process according to the invention, have particularly favorable properties when used for the preservation and/or stabilization of materials containing cellulose fibers. Further, alkoxides according to claim 1 and alkoxides prepared according to the process of claims 2 to 9 and their solutions are particularly suitable to be employed in the preparation of catalysts for the polymerization of olefins.

Thus, the present invention relates to solutions of alkoxides containing titanium and/or zirconium and/or hafnium and magnesium and/or calcium and/or strontium and/or barium having the general formula I $$[M^{II}(OR)_{2-y}(OR^1)_y]_n \cdot [M^{IV}(OR^1)_{4-z}(OR)_z] \qquad (I)$$

wherein

M$^{II}$ represents magnesium and/or calcium and/or strontium and/or barium; and M$^{IV}$ represents titanium and/or zirconium and/or hafnium;

R is an alkyl residue of from 1 to 18 carbon atoms; and

R$^1$ is an alkyl residue of from 1 to 18 carbon atoms;

y takes a value of from 0 to 2; and z takes a value of from 0 to 4; and n is a number of between 0.001 and 3, with the proviso that n is not 1, when y is 2 and z is 0 or y is 0 and z is 4.

Alkoxides of general formula I generally include compounds corresponding to a composition such as

[Mg(C$_2$H$_5$O)$_2$]·[Ti(C$_2$H$_5$O)$_3$(i—C$_3$H$_7$O)] (magnesium titanium (1:1) ethylate isopropylate); or

[Mg$_{0.5}$Ca$_{0.5}$(CH$_3$O)$_2$]$_{0.3}$·[Ti(CH$_3$O)$_4$] (magnesium/calcium titanium (0.3:1) methylate); or

[Mg(C$_2$H$_5$O)$_2$]$_{1.75}$·[Zr(n-C$_8$H$_{17}$O)$_4$] (magnesium zirconium (1.75:1) ethylate n-octylate); or

[Ba(C$_2$H$_5$O)$_2$]·[Ti$_{0.9}$Zr$_{0.1}$(i—C$_4$H$_9$O)$_4$] (barium titanium/zirconium (1:1) ethylate i-butylate).

The present invention further relates to a process for the preparation of alkoxides containing magnesium and/or calcium and/or strontium and/or barium and titanium and/or zirconium and/or hafnium, characterized in that alkoxides of general formula I

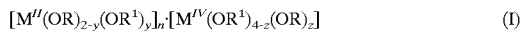
$$[M^{II}(OR)_{2-y}(OR^1)_y]_n \cdot [M^{IV}(OR^1)_{4-z}(OR)_z] \qquad (I)$$

wherein M$^{II}$ represents magnesium and/or calcium and/or strontium and/or barium, and M$^{IV}$ represents titanium and/or zirconium and/or hafnium, R is an alkyl residue of from 1 to 18 carbon atoms and R$^1$ is an alkyl residue of from 1 to 18 carbon atoms, y takes a value of from 0 to 2 and z takes a value of from 0 to 4, and n is a number of between 0.001 and 3;

are obtained by reacting at least one alkoxide of the elements magnesium and/or calcium and/or strontium and/or barium with at least one alkoxide of the elements titanium and/or zirconium and/or hafnium at a temperature which is in the range of the decomposition temperature of at least one of the alkoxides employed.

In the process according to the invention, at least one alkoxide of the elements magnesium and/or calcium and/or strontium and/or barium is reacted with at least one alkoxide of the elements titanium and/or zirconium and/or hafnium suitably in a molar ratio of from 0.001 to 3:1, preferably in a molar ratio of from 0.5 to 1.5:1.

Generally, the alkoxides are mixed as a suspension or powder within the above mentioned range of molar ratios to give an essentially homogeneous mixture, and subsequently heated to the reaction temperature. The process according to the invention is preferably performed to form a homogeneous phase in the reaction.

The reaction is preferably performed in the presence of at least one inert fluxing agent. As the fluxing agent, there may be employed hydrocarbons, for example, pentane, hexane, heptane, and/or liquid fluorohydrocarbons, for example, 1-perfluorohexane and perfluoro-2-methylpentane, and/or alcohols, for example, ethanol, and/or organosiloxanes, for example, hexamethyl-disiloxane, or mixtures thereof.

For the reaction in the process according to the invention, the ratio of alkoxides to fluxing agents can be adjusted to from 99.9% by weight :0.1% by weight to 0.1% by weight :99.9% by weight.

The reaction can be performed at a temperature between 105 and 200° C., preferably from 120 to 190° C., more preferably between 140 and 170° C.

In the process according to the invention, the reaction of the alkoxides employed is preferably performed for a period of from 1 to 8 hours. This usually gives the objective products in almost quantitative yields.

The alkoxide obtained by the reaction can be adjusted to a concentration of from >0 to 90% by weight by adding solvents.

The application as a precursor for the preparation of catalysts for the polymerization of olefins conveniently employs a solution of the alkoxides prepared according to the invention in hydrocarbons, preferably in hexane and/or heptane.

The present invention also relates to the use of the alkoxides according to claim 1 and of the alkoxides prepared according to claims 2 to 9 and their solutions for the preparation of catalysts for the polymerization of olefins.

The present invention further relates to the use of the alkoxides according to claim 1 for the preservation and/or stabilization of materials containing cellulose fibers.

The application as preservatives for cellulose-containing materials may advantageously employ fluorohydrocarbons, especially 1H-perfluorohexane and perfluoro-2-methylpentane, as well as methyl siloxanes and hexamethyldisiloxane as readily evaporable solvents.

Therefore, the present invention also relates to the use of the alkoxides according to claim 1 in solvents or as an emulsion for the preservation and/or stabilization of cellulose-containing materials.

The use of such solvents in connection with the alkoxides prepared according to the invention is particularly advantageous if the compounds of general formula I contain magnesium and titanium, and the alkoxides contain ethyl and isopropyl groups as organic residues; this gives a noticeable stabilization effect in the treated paper. Suitably, the main fraction of the alkoxides of general formula I according to the invention is incorporated in the paper rather than being separated as white powdery titanium dioxide, as has been observed previously. This surprising effect which is achieved simultaneously with the neutralization of the paper causes an additional mechanical stabilization of the paper in the same process step. In addition, a hydrophobizing finish of materials containing cellulose fibers can be achieved at the same time, which means an additional protection, e.g., from intruding moisture which may also be loaded with harmful substances.

The invention will be further illustrated by means of the following Examples.

EXAMPLE 1

Preparation of Magnesium Titanium (1:1) Ethylate

In a 2 l laboratory glass reactor equipped with a stirrer, dropping funnel (500 ml), reflux condenser (0.2 m$^2$) and internal thermometer, heated by a double jacket and circulation thermostat, 1 mol (228.1 g) of solid tetraethoxytitanium and 1 mol (114.4 g) of solid diethoxymagnesium were charged under exclusion of atmospheric oxygen and moisture, and heated at 140° C. for 6 hours with slow stirring. A clear, slightly yellow viscous liquid formed which, after cooling to 100° C., was dissolved in 342 g (560 ml) of cold n-heptane to give a clear solution.

The 50% solution in heptane had a density D$_4^{20}$ of 0.841 g/ml and a viscosity of 1.83 mPa·s (20° C.).

Analysis:

found: Mg 3.5%; Ti 6.9%;

calculated: Mg 3.55%; Ti 6.99%.

Comparative Example for Example 1

Twenty-three grams of tetraethoxytitanium and 11.5 g of diethoxymagnesium were suspended in 56 ml of n-heptane and heated under reflux for 72 hours with stirring at an internal temperature of 102–103° C. The resulting suspension was filtered at 46° C. The filtrate consisted of a solution of tetraethoxytitanium in heptane and did not contain any magnesium. The filtration residue consisted of unchanged magnesium ethylate. Thus, no association had occurred between the two metal alcoholates.

EXAMPLE 2

Preparation of Magnesium Titanium (2:1) Ethylate Butylate

In a 700 l tank equipped with an anchor agitator, reflux condenser, dosing receivers for liquids and a gated lock for the addition of free-flowing solids, 37.0 kg (324 mol) of diethoxymagnesium was mixed with 55.0 kg (162 mol) of tetra-n-butoxytitanium under completely inert conditions and heated at 162° C. for 8 hours with slow stirring. A clear, slightly yellow low-viscous liquid formed. Then, 218 kg of hexane was stirred in within 3–4 hours while the temperature was maintained at 80–85° C. (some refluxing of the hexane occurred). After cooling to 20° C., a slight turbidity from magnesium hydroxide was filtered off (flow rate 200 l/h). The 30% solution was found to weigh 308 kg (99.4% yield)

Analysis:

found: $TiO_2$ 4.08%; Mg 2.59%;

calculated: $TiO_2$ 4.20%; Mg 2.56%.

EXAMPLE 3

Preparation of Magnesium Zirconium (1:1) Ethylate n-propylate

In a 1 l laboratory reactor equipped as in Example 1, 26.7 g (0.233 mol) of diethoxymagnesium and 76.4 g (0.233 mol) of tetra-n-propoxyzirconium (prepared from commercially available solution in n-propanol by drying) were slowly stirred together with 5 g of n-heptane for 5 hours at 143° C. under completely inert conditions. An orange-brown viscous liquid formed which was converted to a clear orange-yellow solution by slowly adding 112 g of n-heptane at 108–109° C.

This 47% solution in heptane had a density $D_4^{20}$ of 0.849 g/ml and a viscosity of 13.26 mpa·s.

Analysis:

found: Zr 9.6%; Mg 2.4%;

calculated: Zr 9.7%; Mg 2.6%.

EXAMPLE 4

Preparation of Magnesium Zirconium (2.2:1) n-propylate

By analogy with Example 3, 47.0 g (0.33 mol) of di-n-propoxymagnesium and 49.1 g (0.15 mol) of tetra-n-propoxyzirconium were treated in the presence of 7 g of perfluorodiisobutene. An orange-brown viscous liquid formed which was converted to a 40% clear light-orange solution by slowly adding another 137 g of isooctane at 105–106° C.

Analysis:

found: Zr 5.72%; Mg 3.36%;

calculated: Zr 5.69%; Mg 3.34%.

EXAMPLE 5

Preparation of Magnesium Zirconium (1.8:1) Ethylate n-hexylate

By analogy with Example 3, 22.9 g (0.20 mol) of diethoxymagnesium and 55.3 g (0.111 mol) of tetra-n-hexyl zirconate were reacted at 144° C. within 4 hours, and the resulting light-brown viscous liquid was dissolved in 342 g of n-heptane to give a clear light-brown 18.6% solution. Upon cooling, the solution congeals to a greenish gel which is liquified again by heating to 80° C.

Analysis:

found: Zr 2.50%; Mg 1.20%;

calculated: Zr 2.42%; Mg 1.16%.

EXAMPLE 6

Preparation of Magnesium Zirconium (1.75:1) Ethylate n-octylate

By analogy with Example 3, 42.6 g (0.701 mol) of tetra-n-octyl zirconate was reacted with 14 g (0.1224 mol) of magnesium diethylate at 152° C. within 2.5 hours, and the resulting yellow viscous liquid was dissolved in 342 g of n-heptane to give a slightly yellow 14% solution which remained liquid at room temperature.

Analysis of the 14% solution:

found: Zr 1.60%; Mg 0.73%;

calculated: Zr 1.58%; Mg 0.74%.

Solutions with higher concentrations (e.g., 18%) became extremely viscous or gel-like (e.g., 22%) at room temperature.

Evaporating the 14% solution in a rotary evaporator and drying under vacuum gave a solid.

Analysis:

found: Zr 11.3%; Mg 5.2%;

calculated: Zr 11.3%; Mg 5.3%.

The above solid could be redissolved in hexane and hexamethyldisiloxane to give a clear solution at test concentrations of 10% each.

EXAMPLE 7

Preparation of Magnesium Hafnium (1:1) n-butylate

By analogy with Example 3, 47.1 g (0.1 mol) of tetra-n-butyl hafnate was reacted with 17.0 g (0.1 mol) of di-n-butoxymagnesium at 157° C. within 6 hours in the presence of 5 g of hexamethyldisiloxane. The resulting orange-yellow viscous liquid was diluted in another 188 g of hexamethyldisiloxane at 104–105° C. within 2 hours to give a 25% clear solution.

Analysis:

found: Hf 7.10%; Mg 0.90%;

calculated: Hf 6.96%; Mg 0.95%.

EXAMPLE 8

Preparation of Calcium Titanium (1:1) Isobutylate

By analogy with Example 3, 34.0 g (0.1 mol) of tetra-i-butyl titanate was reacted with 18.6 g (0.1 mol) of calcium diisobutylate without a fluxing agent at 164° C. within 8 hours, and the resulting clear slightly yellow viscous liquid was converted to a slightly yellow 66% emulsion by stirring in 28 g of perfluorodipropene at 50° C.

Analysis:
found: Ti 5.80%; Ca 5.20%;
calculated: Ti 6.00%; Ca 5.02%.

EXAMPLE 9

Preparation of Magnesium Titanium (1:1) Ethylate Isopropylate

By analogy with Example 2, 30.0 kg (262.2 mol) of diethoxymagnesium and 63.5 kg (262.2 mol) of an orthotitanic acid ester with 75% of ethoxy and 25% of isopropoxy groups as the ester components were reacted at 169° C. for 8 hours in the presence of 200 g of active charcoal. At 103–104° C., 218 kg of hexamethyldisiloxane was metered in, and the resulting solution was filtered at 20° C. There was obtained 303.5 kg (97.5% yield) of a clear colorless low-viscous 30% solution.

Analysis:
found: $TiO_2$ 6.90%; Mg 2.00%;
calculated: $TiO_2$ 6.72%; Mg 2.05%.

EXAMPLE 10

Stabilization and Preservation of Over 90 Years Old Paper in Printing Products With Magnesium Titanium (1:1) Ethylate Isopropylate From Example 9

From the "Gesetzes- und Verordnungsblatt für das Großherzogtum Baden", annual 1900, several test strips sized 5×40 mm were carefully cut from an empty page.

The slightly browned paper showed evident traces of ageing, was easily torn and was no longer resistant to folding. The pH was about 5.0, and the moisture content was around 3–4%.

Nine untreated original test strips were folded over end-to-end for 300 seconds and loaded with a 100 g weight. The weight was then removed, and after another 30 minutes, the return angle was measured by which the crease had reopened in this period. This measurement showed that seven samples reopened the crease to angles of from 12 to 49 degrees. Two samples did not open the creases any more. All samples exhibited many fiber breaks.

A vacuum of about 2 mbar was applied to 14 other untreated original test strips in a Schlenk tube with a volume of 100 ml at 25° C. The vacuum was released by flooding with a 6% solution of magnesium titanium (1:1) ethylate isopropylate (Example 9) in hexamethyldisiloxane, and the Schlenk tube was heated unpressurized to an interior temperature of 56° C. by means of a thermostat. After a total of 20 minutes, the liquid was pressed out again with nitrogen, the sample was again completely evacuated, and the vacuum released with nitrogen.

The samples were allowed to stand in Petri dishes over night. Then, nine of the treated test strips were subjected to the same folding test as described above for the untreated samples. All treated samples reopened the crease to angles of over 90 degrees, two of them even reached 180 degrees. The samples showed only a few fiber breaks. Titanium dioxide was also hardly visible. An acidic pH could no longer be detected, and the moisture content was below 0.1%.

In Addition to Example 10 use of calcium titanium (1:1) isobutylate instead of the magnesium titanium (1:1) ethylate isopropylate used in Example 10

By analogy with Example 10, nine untreated original test strips were treated in a Schlenk tube with a 6% solution of calcium titanium (1:1) isobutylate in hexamethyldisiloxane. The crease of the treated samples reopened to angles of from 12 to 72 degrees. Fiber breaks could be seen with all samples, and all samples were distinctly covered with titanium dioxide powder. An acidic pH was no longer detectable.

What is claimed is:

1. A process for the preparation of alkoxides of the general formula I $$[M^{II}(OR)_{2-y}(OR^1)_y]_n \cdot [M^{IV}(OR^1)_{4-z}(OR)_z] \qquad (I)$$

wherein $M^{II}$ represents magnesium and/or calcium and/or strontium and/or barium, and $M^{IV}$ represents titanium and/or zirconium and/or hafnium, R is an alkyl residue of from 1 to 18 carbon atoms and $R^1$ is an alkyl residue of from 1 to 18 carbon atoms, y takes a value of from 0 to 2 and z takes a value of from 0 to 4, and n is a number between 0.001 and 3;

by reacting at least one alkoxide of the elements magnesium and/or calcium and/or strontium and/or barium with at least one alkoxide of the elements titanium and/or zirconium and/or hafnium at a temperature which is in the range of the decomposition temperature of at least one of the alkoxides employed.

2. The process according to claim 1, characterized in that at least one alkoxide of the elements magnesium and/or calcium and/or strontium and/or barium is reacted with at least one alkoxide of the elements titanium and/or zirconium and/or hafnium in a molar ratio of from 0.001:1 to 3:1.

3. The process according to claims 1 or 2, characterized in that a homogeneous phase is formed in the reaction.

4. The process according to claim 1, characterized in that the reaction is carried out in the presence of at least one inert fluxing agent.

5. The process according to claim 4, characterized in that the fluxing agents used are hydrocarbons and/or liquid fluorohydrocarbons and/or alcohols and/or organosilanes and/or organosiloxanes or mixtures thereof.

6. The process according to claims 4 or 5, characterized in that for the reaction, the ratio of alkoxides to fluxing agents is adjusted to a value from 99.9% by weight:0.1% by weight to 0.1% by weight :99.9% by weight.

7. The process according to claim 1, characterized in that the reaction is performed at a temperature between 105 and 200° C.

8. The process according to claim 1, characterized in that the alkoxide obtained by the reaction is adjusted to a concentration of from >0 to 90% by weight by the addition of solvents.

* * * * *